United States Patent
Chang et al.

(10) Patent No.: US 9,688,776 B2
(45) Date of Patent: Jun. 27, 2017

(54) ANTI-HUMAN MIGA ANTIBODIES CAPABLE OF LYSING MIGA-B LYMPHOCYTES AND DECREASING IGA PRODUCTION

(71) Applicant: Immunwork Inc., Taipei (TW)

(72) Inventors: Tse-Wen Chang, Taipei (TW); Alfur Fu-Hsin Hung, Taichung (TW); Donic Chien-Sheng Lu, Kaohsiung (TW)

( * ) Notice: Subject to any disclaimer, the term of this patent is extended or adjusted under 35 U.S.C. 154(b) by 0 days.

(21) Appl. No.: 15/172,170

(22) Filed: Jun. 3, 2016

(65) Prior Publication Data

US 2016/0289339 A1   Oct. 6, 2016

Related U.S. Application Data

(63) Continuation of application No. PCT/CN2014/001097, filed on Dec. 5, 2014.

(60) Provisional application No. 61/912,395, filed on Dec. 5, 2013.

(51) Int. Cl.
*A61K 39/395* (2006.01)
*C07K 16/42* (2006.01)
*C07K 14/395* (2006.01)
*A61K 39/00* (2006.01)

(52) U.S. Cl.
CPC ........ *C07K 16/4283* (2013.01); *C07K 14/395* (2013.01); *A61K 2039/505* (2013.01); *C07K 2317/24* (2013.01); *C07K 2317/52* (2013.01); *C07K 2317/56* (2013.01); *C07K 2317/565* (2013.01); *C07K 2317/73* (2013.01); *C07K 2317/732* (2013.01); *C07K 2319/03* (2013.01); *C07K 2319/30* (2013.01); *C07K 2319/73* (2013.01)

(58) Field of Classification Search
None
See application file for complete search history.

(56) References Cited

U.S. PATENT DOCUMENTS

| 5,079,344 A * | 1/1992 | Chang | A61K 47/48284 435/337 |
| 5,089,603 A * | 2/1992 | Chang | A61K 47/48284 435/70.21 |
| 5,281,699 A * | 1/1994 | Chang | C07K 16/30 530/324 |

OTHER PUBLICATIONS

Rai et al., J Am Soc Nephrol. Dec. 1999;10(12):2637-44.*
Papista et al., Cell Mol Immunol. Mar. 2011;8(2):126-34. doi: 10.1038/cmi.2010.69. Epub Jan. 31, 2011.*

* cited by examiner

*Primary Examiner* — Michael Szperka

(57) ABSTRACT

Disclosed herein is an anti-migis-αα antibody specific for the migis-α of human mα chain that can bind to mIgA on B lymphocytes, cause the lysis of mIgA-expressing B lymphocytes, and decrease IgA production by IgA-secreting B lymphocytes. Disclosed further is a pharmaceutical composition comprising the anti-migis-α antibody and a pharmaceutically acceptable carrier. Disclosed further is a method for lysing mIgA-expressing B lymphocytes and reducing IgA production in a human subject in vivo by employing an antibody specific for the migis-α of human mα chain that can bind to mIgA on B lymphocytes, cause the lysis of mIgA-expressing B lymphocytes, and decrease IgA production by IgA-secreting B lymphocytes. Disclosed herein is also a method for treating a disease in a subject, comprising administering to the subject an antibody specific for the migis-α of human mα chain that can bind to mIgA on B lymphocytes, thereby lysing mIgA-expressing B lymphocytes and reducing IgA production in the immune system of the subject. In addition, Disclosed also is use of said anti-migis-α antibody or said fragment thereof for treating a disease in a subject that can benefit from the elimination of mIgA-expressing cells or the reduction of IgA antibodies in the immune system.

14 Claims, 13 Drawing Sheets

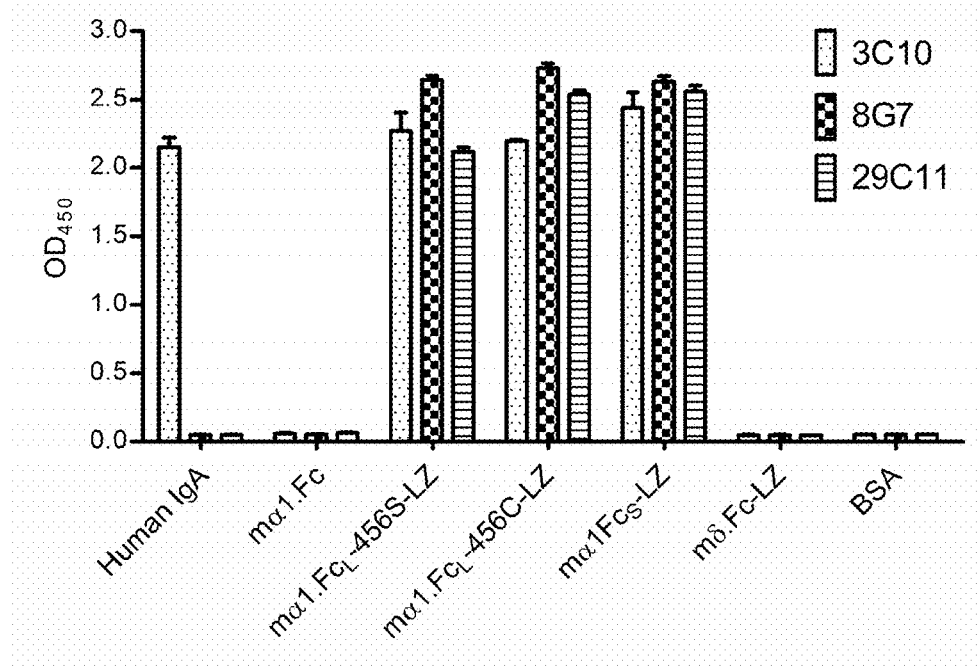

FIG. 3A
| | |
|---|---|
| maFL | DRLAGSCSVADWQMPPPYVVLDLPQETLEEETPGAN |
| maFa | GSCSVADWQMPPPYVVLD |
| maFb | QMPPPYVVLDLPQETL |
| maFc | LDLPQETLEEETPGAN |
| maF1-2 | GSCSVADWQMPP |
| maF1-3 | CSVADWQMPPPY |
| maF2 | VADWQMPPPYVV |
| maF2-1 | DWQMPPPYVVLD |
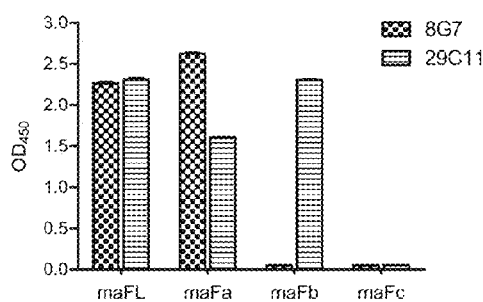
FIG. 3B
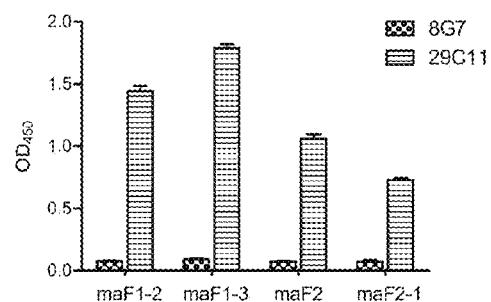
FIG. 3C

8G7 VH

EVQLQESGPSLVKPSQTLSLTCSVTGDSITNGYWNWIRKFPGNKLEYMGY
ISYSGSTYYNPSLKSRIFITRDTSKNQYYLQLNSVTTEDTAIYYCARWLG
GRAYWGQGTTLIVSS

8G7 VL

DIVMTQSQKFMSTSVGDRVSVTCKASQNVGTNVVWYQQKPGQSPKTLIYS
ASRRFSGVPDRFTGSGSGTDFTLTISNVQSEDLAEYFCQQYNSYPLTFGA
GTKLELK

QIQLVQSGPELKKPGETVKISCKASGYTFTNYGMIWVKQAPGKGLKWMGW
INTYTGKPTYADDFKGRFAFSLETSASTAYLQINNLKTEDTATYFCARSN
FREDWCFDVWGAGTTVTVSS

29C11 VL

QIVLTQSPAIMSASPGEKVTMTCSASSSVSYMHWYQQKSGTSPKRWIYDT
SKLASGVPARFSGSGSGTSYSLTISSMEAEDAATYYCQQWSSNPPTFGSG
TKLEIK

FIG. 13

ANTI-HUMAN MIGA ANTIBODIES CAPABLE OF LYSING MIGA-B LYMPHOCYTES AND DECREASING IGA PRODUCTION

STATEMENT OF RELATED APPLICATION

This application is a continuation application of International patent application No. PCT/CN2014/0001097 filed on Dec. 5, 2014, which claims priority to U.S. Provisional Application No. 61/912,395 filed on Dec. 5, 2013, the contents of which are incorporated herein by reference in their entirety.

BACKGROUND OF THE INVENTION

Technical Field

The invention relates to antibodies, particularly, to those capable of binding to human mIgA-expressing B cells.

Description of Related Art

Human IgA has two subclasses, IgA1 and IgA2, respectively, and the IgA1 subclass is predominant in serum (approximately 80%). IgA1 and IgA2 contain the heavy chains α1 and α2, respectively. Both Most α1 and α2 have a secretory (a) and membrane-bound (ma) forms that are translated from two different sets of mRNA derived from the same RNA transcript, with the mRNA of ma containing a membrane exon. Most serum IgA are monomeric forms (around 90%) rather than dimeric or multimeric forms abundant in secretions.

Secretory IgA (SIgA) is the most abundant immunoglobulin present in external secretions. It serves as the humoral immunity against invading microorganisms at the mucosal surface and maintains the balance of dietary antigens in gastrointestinal ducts. SIgA produced by local plasma cells beneath the epithelium layer is in predominantly dimeric or multimeric forms in association with a J chain. Through interaction with polymeric Ig receptors (pIgR) on the basolateral membrane of epithelial cells, SIgA are transported into the lumen by transcytosis after the apical cleavage of pIgR. The cleaved pIgR, known as secretory component, is capable of protecting SIgA from digestion by numerous bacterial proteases at mucosa. It is estimated that about three to five grams of SIgA are secreted in the intestinal lumen each day which can account for its primary role in the regulation of mucosal immune systems.

In addition to secreted forms, IgA exists in a membrane-anchoring form (mIgA) which is encoded by joining a membrane exon after the CH3 exon by RNA splicing. The membrane exon is translated into a membrane-anchoring peptide which corresponds to three different environmental segments, an extracellular peptide, referred to as the mIg isotype-specific (migis-α) segment consisting of 26-32 amino acid residues, a transmembrane region, and a cytosolic tail, respectively. The migis-α segment is varied in sequences and lengths among five Ig isotypes while the transmembrane domain of them is highly conserved. Therefore, the migis-α segment can be served as an antigenic site for targeting mIgA and mIgA-expressing B cells. The resultant antibodies therefore can be used for treating relevant diseases, which can benefit from the elimination of mIgA-expressing cells or the reduction of IgA antibodies in the immune system, such as IgA lymphoctyes, IgA nephropathy (IgAN), Henoch-Schönlein purpura (HSP), Celiac disease, etc.

In IgA1, not IgA2, two splicing acceptor sites are present in the membrane exon and isoforms of mα1 mRNAs are generated by alternative joining of the donor in the CH3 exon towards either acceptor in the membrane exon. Two resultant isoforms differ in that the long isoform ($m\alpha1_L$) has extra six amino acid residues at the N-terminal of migis peptide which is 26 a. a. residues in length for the short isoform ($m\alpha1_S$). The expression amount of $m\alpha1_L$ is about twice more than that of $m\alpha1_S$ in mIgA1-expressing B cells. In studies, two mα1 alleles can produce the long and the short isoforms of migis-α, and three mα2 alleles produce the short form exclusively.

While migis-α has been proposed as an antigenic site for preparing antibodies that can bind to mIgA and cause the lysis of mIgA-expressing B cells since as early as 1990 (U.S. Pat. No. 5,079,334), no such antibodies have ever been prepared. In our previous paper [Hung et al., *Mol. Immunol.* 48(15-16): 1975-1982 (2011)], a number of mAbs that bind strongly to synthetic migis-α polypeptides and to migis-α-containing recombinant proteins in ELISA were prepared. However, among those mAbs, only one, denoted as 29C11, had a marginally detectable binding to mIgA on B cell lines, such as IgA1-expressing DAKIKI cells or Daudi cells transfected with mα1 chains. There were no data provided concerning whether 29C11 can induce lysis of mIgA-expressing B cells by apoptosis, ADCC, or other mechanisms.

SUMMARY OF THE INVENTIONS

In a first aspect, embodiments disclosed herein provide an anti-migis-α antibody or a fragment thereof specific for the migis-α of human mα chain that can bind to mIgA on B lymphocytes, thereby causing the lysis of mIgA-expressing B lymphocytes, and decreasing IgA production by IgA-secreting B lymphocytes.

In some embodiments, the anti-migis-α antibody or the fragment thereof disclosed herein comprises the following complementary-determining regions (CDRs):
(a) the CDR-H1 is residues 26-33 of SEQ ID NO:17,
(b) the CDR-H2 is residues 51-57 of SEQ ID NO:17,
(c) the CDR-H3 is residues 96-104 of SEQ ID NO:17,
(d) the CDR-L1 is residues 27-32 of SEQ ID NO:18,
(e) the CDR-L2 is residues 50-52 of SEQ ID NO:18, and
(f) the CDR-L3 is residues 89-97 of SEQ ID NO:18.

In some embodiments, the anti-migis-α antibody or the fragment thereof comprises VH set forth in SEQ ID NO:17 and VL set forth in SEQ ID NO:18.

In a particular embodiment, the anti-migis-α antibody is MAb 8G7.

In certain embodiments, the antibody or the fragment thereof disclosed herein comprises or is an F(ab)'$_2$, an Fab, an Fv, or a single-chain Fv fragment of the above anti-migis-α antibodies.

In a second aspect, embodiments disclosed herein provide a pharmaceutical composition comprising an anti-migis-α antibody or a fragment thereof specific for the migis-α of human mα chain that can bind to mIgA on B lymphocytes, thereby causing the lysis of mIgA-expressing B lymphocytes, or decreasing IgA production by IgA-secreting B lymphocytes, and a pharmaceutically acceptable carrier.

In certain embodiments, the pharmaceutical composition disclosed herein is for treating a disease in a subject that can benefit from the elimination of mIgA-expressing cells or the reduction of IgA antibodies in the immune system.

In certain embodiments, the disease is selected from the group consisting of IgA lymphoctyes, IgA nephropathy (IgAN), Henoch-Schönlein purpura (HSP) and Celiac disease.

In a third aspect, embodiments disclosed herein provide a method for lysing mIgA-expressing B lymphocytes and reducing IgA production in a subject in vitro or in vivo comprising employing to the subject an antibody or a fragment thereof specific for the migis-α of human mα chain that can bind to mIgA on B lymphocytes, thereby causing the lysis of mIgA-expressing B lymphocytes, and decreasing IgA production by IgA-secreting B lymphocytes.

In a forth aspect, embodiments disclosed herein provide a method for treating a disease in a subject, comprising administering to the subject an antibody or a fragment thereof specific for the migis-α of human mα chain that can bind to mIgA on B lymphocytes, thereby lysing mIgA-expressing B lymphocytes and reducing IgA production in the immune system of the subject.

In a fifth aspect, embodiments disclosed herein provide use of the anti-migis-α antibody and the fragment thereof disclosed herein for treating a disease in a subject which can benefit from the elimination of mIgA-expressing cells or the reduction of IgA antibodies in the immune system.

In certain embodiments, the disease is selected from the group consisting of IgA lymphoctyes, IgA nephropathy (IgAN), Henoch-Schönlein purpura (HSP) and Celiac disease.

BRIEF DESCRIPTION OF THE DRAWINGS

FIG. 2 is a graph which depicts an ELISA showing the reactivity of an anti-IgA.Fc mAb (3C10) and two anti-migis-α mAbs (8G7 and 29C11) with human IgA and constructs, which contain various human membrane-bound α chain, or other components.

FIG. 3A-3C show epitope mapping of anti-migis-α mAbs in ELISA. A) FIG. 3A shows synthesized peptide segments of migis-$α_L$, including maFL (SEQ ID NO:9), maFa (SEQ ID NO:10), maFb (SEQ ID NO:11), maFc (SEQ ID NO:12), maF1-2 (SEQ ID NO:13), maF1-3 (SEQ ID NO:14), maF2 (SEQ ID NO:15), and maF2-1 (SEQ ID NO:16). Underlined sequences are from the CH3 domain of IgA. B) FIG. 3B shows binding reactivity of anti-migis-α mAbs with different parts of migis-$α_L$. C) FIG. 3C shows binding reactivity of anti-migis-α mAbs with short peptides of the N-terminal part of migis-$α_L$.

FIG. 4A shows binding strength of 8G7 and 29C11 against mα1.Fc$_L$-456S-LZ proteins. A) FIG. 4B. shows relative ability of 8G7 and 29C11 in competing with 200 nM biotin-conjugated 29C11 in binding to Fc$_L$-456S-LZ protein.

FIG. 10A shows that c8G7 can significantly and specifically decrease the IgA production by human PBMCs. , p<0.05; *p<0.001. B) FIG. 10B shows that IgA levels in the c8G7-treated group are reduced to 54% of levels in the control group.

FIG. 11A shows surface expression levels of ma1.Fc and B cell markers on the two A20 transfectomas. B) FIG. 11B shows the treating schedule of purified antibodies for tumor-transplanted mice.

FIG. 12 shows variable region sequences of heavy (SEQ ID NO:17) and light (SEQ ID NO:18) chains of 8G7 mAb. The three complementarity-determining regions (CDRs) of each chain are shown in boldface.

FIG. 13 shows variable region sequences of heavy (SEQ ID NO:19) and light (SEQ ID NO:20) chains of 29C11 mAb. The three complementarity-determining regions (CDRs) of each chain are shown in boldface.

DETAILED DESCRIPTIONS OF THE INVENTION

Figure 1:
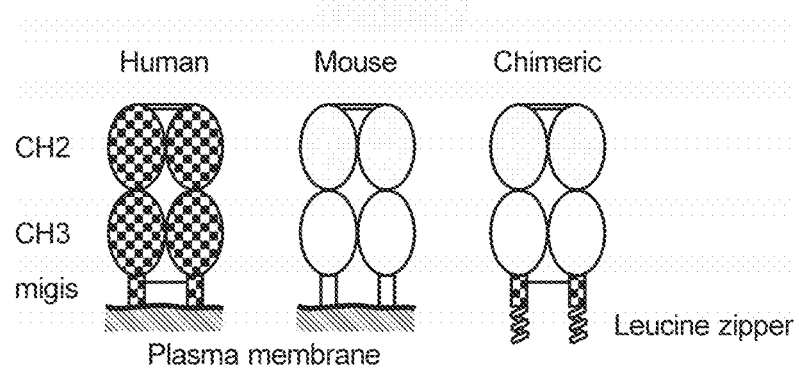
FIG. 1 shows a mouse/human chimeric recombinant protein composing of the CH2 and CH3 domains of murine α immunoglobulin, the migis-α segment of the membrane-anchoring peptide of human membrane-bound α chain, and a leucine zipper peptide, which replaces the transmembrane peptide segment. The peptide forms dimmers.

Membrane-bound IgA (mIgA) is associated with Igα/Igβ as the B cell receptor (BCR) complex on mIgA-expressing B cells. The α chain of mIgA (mα) further contains a C-terminal membrane-anchor peptide compared to α chain of IgA (α), which encompasses extracellular, transmembrane and intracellular segments. The extracellular segment, referred to as the mIg isotype-specific (migis-α) segment or the extracellular membrane proximal domain of mα, is specific to the mα and has been proposed to be specific antigenic site suitable for isotype-specific targeting of mIgA-expressing B cells by antibodies (U.S. Pat. No. 5,079,334), no such antibodies have ever been prepared up to now.

It has been reported that it would seem to indicate that the epitopes present on migis-α on mIgA are not accessible. Many anti-migis-α mAbs can bind to synthetic migis-α-containing peptides or recombinant proteins very strongly in ELISA plate. However, they cannot bind to mIgA on B cells to any detectable extent. Even the identified 29C11 can bind to mIgA on B cells at a detectable extent, such binding is very marginal. These results from the prior art would suggest that the antigenic sites on migis-α on mIgA on B cells exist in certain native conformations or are interfered by certain adjacent molecules, so that they are not accessible by antibodies [Hung et al., *Mol. Immunol.* 48(15-16): 1975-1982 (2011)].

In the present application, we rationalize that a synthetic migis-α peptide cannot present native conformation and therefore cannot induce antibodies that recognize migis-α in its native conformation. We further rationalize that while proteins with CH3 and migis-α of human mα can present native conformation on migis-α, such an epitope is blocked by antibodies recognizing adjacent CH3 domain of mIgA during an immunization process, and the B lymphocytes with antibody receptor specific for the migis-α epitope do not get a chance to bind to the migis-α epitope. Based on this hypothesis, we design an immunogen that would eliminate such a complication. Specifically, such an immunogen contains CH3 of murine origin and human migis-α. In the immunized mice, no antibodies would be induced to bind to CH3, which is a self antigen, allowing the migis-α in its native conformation to be recognized by B cells carrying the antibody receptors that are specific for migis-α. Using this strategy, we have generated migis-α mAbs that can recognize mIgA on B cells with much superior binding capability. We have shown that the migis-α mAbs can bind to mIgA-expressing B cells and cause the cytolysis of those B cells by apoptosis in the presence of secondary cross-linking antibody, while 29C11 cannot. We further showed that the migis-α mAbs can trigger the cellular cytotoxicity with human peripheral blood mononuclear cells (PBMCs) and decrease the IgA production of human PBMCs in vitro.

In a first aspect, embodiments disclosed herein provide an isolated anti-migis-α antibody or a fragment thereof specific for the migis-α of human mα chain that can bind to mIgA on B lymphocytes, thereby causing the lysis of mIgA-expressing B lymphocytes, and decreasing IgA production by IgA-secreting B lymphocytes.

In some embodiments, the anti-migis-α antibody or the fragment thereof disclosed herein comprise the following complementary-determining regions (CDRs):
(a) the CDR-H1 is residues 26-33 of SEQ ID NO:17,
(b) the CDR-H2 is residues 51-57 of SEQ ID NO:17,
(c) the CDR-H3 is residues 96-104 of SEQ ID NO:17,
(d) the CDR-L1 is residues 27-32 of SEQ ID NO:18,
(e) the CDR-L2 is residues 50-52 of SEQ ID NO:18, and
(f) the CDR-L3 is residues 89-97 of SEQ ID NO:18.

In some embodiments, the anti-migis-α antibody or the fragment thereof comprises VH set forth in SEQ ID NO:17 and VL set forth in SEQ ID NO:18.

By "isolated" is meant the removal of a protein from its natural environment. It is to be understood, however, that proteins may be formulated with diluents or adjuvants and still for practical purposes be isolated. For example, antibodies typically are mixed with an acceptable carrier when used for treating a disease.

Typically, an immunoglobulin has a heavy and light chain. Each heavy and light chain contains a constant region and a variable region (VH and VL, respectively), (the regions are also known as "domains"). Light and heavy chain variable regions contain a "framework" region interrupted by three hypervariable regions, also called "complementarity-determining regions" or "CDRs". The extent of the framework region and CDRs has been defined. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a $V_L$ CDR1 is the CDR1 from the variable domain of the light chain of the antibody in which it is found.

In one embodiment, the anti-migis-α antibody or the fragment thereof is a chimeric, humanized, or human antibody.

Generally, a humanized antibody has one or more amino acid residues introduced into it from a source that is non-human. These non-human amino acid residues are often referred to as import residues, which are typically taken from an import variable domain. Humanization can be essentially performed following the methods described in Jones et al., Nature 321:522-525 (1986); Riechmann et al., Nature 332:323-327 (1988); or Verhoeyen et al., Science 239:1534-1536 (1988), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some embodiments, "human antibody" refers to an immunoglobulin comprising human hypervariable regions in addition to human framework and constant regions. Such antibodies can be produced using various techniques known in the art. For example in vitro methods involve use of recombinant libraries of human antibody fragments displayed on bacteriophage (e.g., McCafferty et al, 1990, Nature 348:552-554; Hoogenboom & Winter, J. Mol. Biol. 227:381 (1991); and Marks et al, J. Mol. Biol. 222:581 (1991)), yeast cells (Boder and Wittrup, 1997, Nat Biotechnol 15:553-557), or ribosomes (Hanes and Pluckthun, 1997, Proc Natl Acad Sci USA 94:4937-4942). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 6,150,584, 5,545,807; 5,545,806; 5,569,825; 5,625,126; 5,633,425; 5,661,016, and in the following scientific publications: (e.g., Jakobavits, Drug Deliv Rev. 31:33-42 (1998), Marks et al, Bio/Technology 10:779-783 (1992); Lonberg et al, Nature 368:856-859 (1994); Morrison, Nature 368:812-13 (1994); Fishwild et al, Nature Biotechnology 14:845-51 (1996); Neuberger, Nature Biotechnology 14:826 (1996); Lonberg & Huszar, Intern. Rev. Immunol. 13:65-93 (1995).

In one specific embodiments, the anti-migis-α antibody is MAb 8G7.

In certain embodiments, the antibody or the fragment thereof disclosed herein comprises or is an F(ab)'₂, an Fab, an Fv, or a single-chain Fv fragment of the above anti-migis-α antibodies.

In some embodiments, "antibody fragments" means molecules that comprise a portion of an intact antibody, generally the antigen binding or variable region of the intact antibody. Examples of antibody fragments include Fab, Fab', F(ab')₂, and Fv fragments; single domain antibodies (see, e.g., Wesolowski, Med Microbiol Immunol. (2009) 198(3): 157-74; Saerens, et al., Curr Opin Pharmacol. (2008) 8(5): 600-8; Harmsen and de Haard, Appl Microbiol Biotechnol. (2007) 77(1): 13-22); helix-stabilized antibodies (see, e.g., Arndt et al., J Mol Biol 312:221-228 (2001); diabodies (see below); single-chain antibody molecules ("scFvs," see, e.g., U.S. Pat. No. 5,888,773); disulfide stabilized antibodies ("dsFvs", see, e.g., U.S. Pat. Nos. 5,747,654 and 6,558,672), and domain antibodies ("dAbs," see, e.g., Holt et al., Trends Biotech 21(11):484-490 (2003), Ghahroudi et al., FEBS Lett. 414:521-526 (1997), Lauwereys et al., EMBO J 17:3512-3520 (1998), Reiter et al., J. Mol. Biol. 290:685-698 (1999), Davies and Riechmann, Biotechnology, 13:475-479 (2001)).

In a second aspect, embodiments disclosed herein provide a pharmaceutical composition comprising an anti-migis-α antibody or a fragment thereof specific for the migis-α of human mα chain that can bind to mIgA on B lymphocytes, thereby causing the lysis of mIgA-expressing B lymphocytes, or decreasing IgA production by IgA-secreting B lymphocytes, and a pharmaceutically acceptable carrier.

The expression "pharmaceutically acceptable" means acceptable for use in the pharmaceutical and veterinary arts, i.e. not being unacceptably toxic or otherwise unsuitable.

In certain embodiments, the pharmaceutical composition disclosed herein is for treating a disease in a subject that can benefit from the elimination of mIgA-expressing cells or the reduction of IgA antibodies in the immune system.

In certain embodiments, the disease is selected from the group consisting of IgA lymphoctyes, IgA nephropathy (IgAN), Henoch-Schönlein purpura (HSP) and Celiac disease.

In a third aspect, embodiments disclosed herein provide a method for lysing mIgA-expressing B lymphocytes and reducing IgA production in a subject in vitro or in vivo comprising employing to the subject an antibody or an fragment thereof specific for the migis-α of human mα chain that can bind to mIgA on B lymphocytes, cause the lysis of mIgA-expressing B lymphocytes, and decrease IgA production by IgA-secreting B lymphocytes.

In a forth aspect, embodiments disclosed herein provide a method for treating a disease in a subject, comprising administering to the subject an antibody or an fragment specific for the migis-α of human mα chain that can bind to mIgA on B lymphocytes, thereby lysing mIgA-expressing B lymphocytes and reducing IgA production in the immune system of the subject.

In certain embodiments, the disease is selected from the group consisting of IgA lymphoctyes, IgA nephropathy (IgAN), Henoch-Schönlein purpura (HSP) and Celiac disease.

In a fifth aspect, embodiments disclosed herein provide use of the anti-migis-α antibody or the fragment thereof disclosed herein for treating a disease in a subject which can benefit from the elimination of mIgA-expressing cells or the reduction of IgA antibodies in the immune system.

In certain embodiments, the disease is selected from the group consisting of IgA lymphoctyes, IgA nephropathy (IgAN), Henoch-Schönlein purpura (HSP) and Celiac disease.

In certain embodiments, the terms "subject" or "patient" disclosed herein are used interchangeably.

In certain embodiments, the term "subject" or "patient" refers to a cell (e.g. an immune cell, a B lymphocyte, or mIgA-expressing B lymphocytes), an animal (e.g., birds, reptiles, and mammals), preferably a mammal including a non-primate (e.g., a camel, donkey, zebra, cow, pig, horse, cat, dog, rat, and mouse) and a primate (e.g., a monkey, chimpanzee, and human). In certain embodiments, the subject or patient can benefit from the elimination of mIgA-expressing cells or the reduction of IgA antibodies in the immune system.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The following examples further illustrate the embodiments but, of course, should not be construed as in any way limiting its scope.

EXAMPLES

Example 1

Construction and Expression of Recombinant Migis-α-Containing Proteins

To prepare the mouse/human chimeric migis-$α_L$-containing protein (SEQ ID NO: 1) for immunizing mice, the human IgA1.Fc portion was replaced by the mouse IgA.Fc and the transmembrane region was replaced by a water-soluble GCN4 leucine zipper (FIG. 1). The DNA sequence encoding this chimeric protein was synthesized by gene synthesis (GeneArt). An extra DNA sequence encoding a mouse kappa chain leader peptide, a poly-His tag, and a linker peptide was incorporated at the 5' terminal of the sequence. The synthesized sequence was cloned into a pcDNA3.1 vector (Invitrogen). The chimeric proteins were expressed by using the FreeStyle™ 293 Expression System (Invitrogen). For large-scale cell transfection, 1.2 mg of plasmid DNA diluted in 20 ml of serum-free DMEM was mixed with 3.6 mg of linear polyethylenimine (Polysciences) diluted in 20 ml of 9 g/L NaCl solution. The mixture was incubated at room temperature for 10 min and then slowly added into $2 \times 10^9$ FreeStyle™ 293F cells resuspended in a culturing flask containing 160 ml of fresh FreeStyle™ 293 expression medium. Cells were shaken at 37° C. for 4 hr and then 600 ml of fresh FreeStyle™ 293 expression medium was added into the flask for further culturing. After cell growing for 5 days, the culture medium was centrifuged and the supernatant was subjected to protein purification by using the Protino® Ni-NTA Agarose (MA-CHEREY-NAGEL). The purification procedure was followed by the manufacturer's manual and the purified proteins were stored in PBS. To prepare recombinant proteins used for enzyme-linked immunosorbent assay (ELISA)

screening and examination of hybridoma clones, DNA sequences encoding various isoforms and alloforms of human migis-α-containing proteins which were mα1.Fc (SEQ ID NO:2) and mα1.Fc$_S$-LZ (SEQ ID NO:3), mα1.Fc$_L$-456S-LZ (SEQ ID NO:4), and Fc$_L$-456C-LZ (SEQ ID NO:5), respectively, were cloned from cDNA prepared from mRNA of DAKIKI cells (ATCC), which is a IgA-expressing B cell line, or human PMBC by PCR. The amplified DNA fragments were further ligated into the modified pcDNA3.1 vector described above. Cell transfection, protein expression, and protein purification for these constructs were followed as described above.

Example 2

Identification of a Novel Anti-Migis-α mAb Capable of Binding to mIgA-Expressing B Cells Significantly Fifty microgram of the chimeric protein was used to immunize each Balb/c mouse subcutaneously for 4-5 times in a two-week interval. Three days before cell fusion, ten microgram of the chimeric protein was injected into each mouse intravenously. The splenocytes isolated from immunized mice were fused with mouse myeloma cells FO by using polyethylene glycol 1500 (Roche). After fusion procedures, cells were grown in HAT selection medium for 10-12 days and the cultured medium was transferred for ELISA screening (detailed in the next section). Recombinant proteins mα1.Fc$_L$-456S-LZ and mα1.Fc were served as positive antigens and negative antigens, respectively. Hybridoma clones which produce antibodies reacting to mα1.Fc$_L$-LZ and not reacting to mα1.Fc were identified as candidates by using horseradish peroxidase (HRP)-conjugated goat anti-mouse IgG.Fc antibodies (Jackson ImmunoResearch) in ELISA. To further test the binding of hybridoma candidates towards mIgA-expressing B cells, $2\times10^5$ DAKIKI cells were incubated with 100 μl of cultured medium on ice for 30 min. Cells were washed with staining buffers [PBS with 2% fetal bovine serum (FBS, Invitrogen) and 0.05% sodium azide] and incubated with FITC-labeled rabbit F(ab)'$_2$ anti-mouse IgG antibodies (AbD Serotech) 1:400 diluted in staining buffers on ice for 30 min. After washing, cells were resuspended in 200 μl of staining buffer and subjected to flow cytometric analyses. In this example a novel anti-migis-α hybridoma 8G7 which could bind significantly to DAKIKI cells was identified. The hybridoma sub-clones were further obtained and characterized by cell cloning procedures.

Example 3

Examination of Binding Reactivity and Relative Binding Affinity of Anti-Migis-α mAbs Anti-migis-α mAbs 8G7 (Igγ2b, κ) and 29C11 (Igγ1, κ) were purified from hybridoma culturing medium by using Protein A Sepharose CL-4B medium (GE Healthcare). Purified mAbs were stored in PBS at the concentration of 1 mg/ml. A mouse anti-human IgA1.Fc mAb 3C10 (Igγ1, Abcam) and mouse total IgG (Sigma-Aldrich) were used as positive and negative controls, respectively. Various migis-α-containing recombinant proteins and several irrelevant proteins were tested in ELISA. Proteins were coated at 1 μg/ml in 0.05M carbonate/bicarbonate buffers in ELISA plates at 4° C. for overnight. Plates were washed with PBST (PBS with 0.05% Tween® 20) and blocked by PBS/BSA (PBS with 1% BSA) at room temperature for 1 h. After washing with PBST, mAbs at 1 μg/ml in PBS/BSA were added into plates and incubated at room temperature for 1 hr. Plates were washed with PBST and then HRP-conjugated goat anti-mouse IgG.Fc antibodies 1:10,000 diluted in PBS/BSA were adding into plates. After incubation at room temperature for 1 hr and washing with PBST, Tetramethylbenzidine substrates (Clinical Scientific Products) were added into plates for colorimetric measurement. FIG. 2 shows that 8G7 specifically reacts to migis-α segments.

Synthetic migis-α$_L$ polypeptides were further used to study binding epitopes of anti-migis-α mAbs by ELISA. Polypeptides maFL (SEQ ID NO:9), maFa (SEQ ID NO:10), maFb (SEQ ID NO:11), and maFc (SEQ ID NO:12) are fragments that represent the full length, the N-terminal part, the middle part, and the C-terminal part of migis-α$_L$ sequences (FIG. 3A). Polypeptides maF1-2 (SEQ ID NO:13), maF1-3 (SEQ ID NO:14), maF2 (SEQ ID NO:15), and maF2-1 (SEQ ID NO:16) were designed to test shorter sequences for binding activity of anti-migis-α mAbs. Polypeptides at 10 μg/ml were coated in micro-well plates for reacting and ELISA procedures were followed as described above. Results show that 8G7 reacts to the N-terminal part of migis-α$_L$ sequences but does not react to short fragments of the N-terminal polypeptide (FIGS. 3B-C). In contrast, 29C11 is capable of binding to both the N-terminal and the middle part of migis-α$_L$ sequences, and also reacting to short fragments of the N-terminal polypeptides. (FIGS. 3B-C).

To determine the relative binding affinity of anti-migis-α mAbs, a serial dilution of mAbs were used to react to mα1.Fc$_L$-456S-LZ proteins and results were quantified by ELISA. The binding curves were analyzed by the software Prism® (GraphPad) and the equation used for calculation was shown below.

$$Y=B_{max}*X/(Kd+X)$$

Figure 4A:
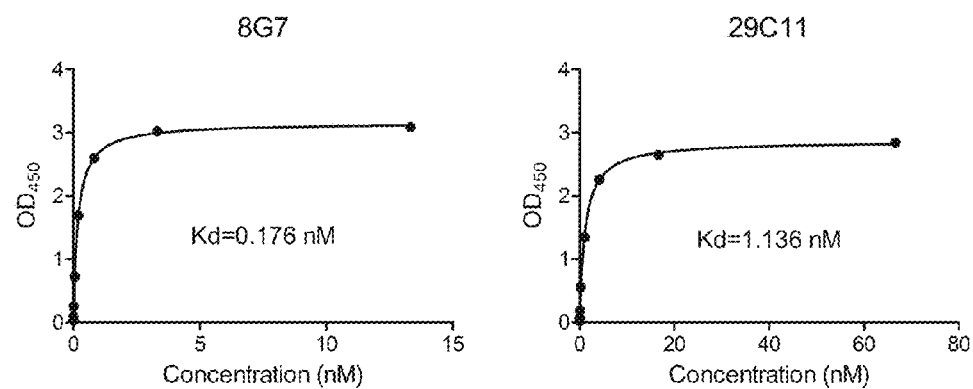
FIG. 4A-4B show determination of the relative affinity of 8G7 and 29C11 in binding to mα in ELISA. A)

$B_{max}$ is the maximum binding in the same unit as Y and Kd is the equilibrium binding constant which is equivalent to the antibody concentration that binds to half the antigens at equilibrium. The concentration of 8G7 reaching half the maximum binding is about six times lower than that of 29C11 (FIG. 4A).

A competition ELISA was also performed to determine capabilities of 8G7 and 29C11 to inhibit the binding of biotin-labeled 29C11 towards mα1.Fc$_L$-456S-LZ proteins. Labeling of biotin to 29C11 was carried out by using the EZ-Link Sulfo-NHS-Biotin and Biotinylation Kit (Thermo Scientific) and procedures were followed according to the manual. In ELISA, mα1.Fc$_L$-456S-LZ proteins were coated at 1 μg/ml in plates which were blocked by PBS/BSA subsequently. A serial 4-fold dilution of 8G7 and 29C11 at a start concentration of 500 nM were pre-mixed with 200 nM biotinylated 29C11, respectively and incubated at room temperature for 20 min. Mixtures were then transferred into plates and incubated at room temperature for 2 hr. After washing, HRP-conjugated avidin (Sigma-Aldrich) 1:100,000 diluted in PBS/BSA were added into plates and incubated for 30 min. After extensive washing, TMB substrates were added for colorimetric measurement. The ELISA results were analyzed by the software Prism® and the value of inhibition concentrations (IC50) of both mAbs were calculated by the equation noticed below.

$$Y=Bottom+(Top-Bottom)/(1+10^{(X-Log\ IC50)})$$

Figure 4B:
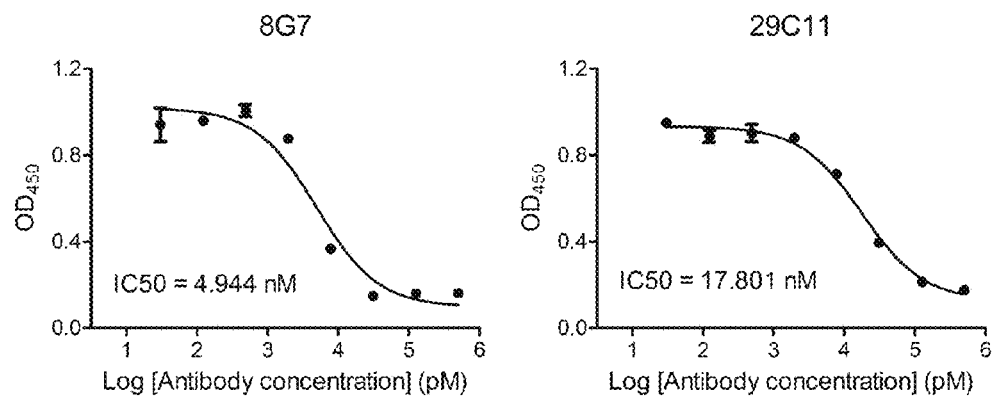

Top and Bottom are plateaus in the units of Y axis and IC50 is the concentration of competitor that results in binding half-way between Bottom and Top. FIG. 4B showed that 8G7 could compete with biotinylated 29C11 binding to migis-α more efficiently than 29C11 did. Results of this example demonstrated that the affinity of 8G7 was higher than that of 29C11.

Example 4

Flow Cytometric Analyses of Anti-Migis-α mAbs Towards mIgA-Expressing B Cells

DAKIKI cells used in hybridoma screening, which express the long and the short isoforms of mα1 chain, were examined by quantitative purified mAbs. To further test the binding towards each individual mα1 isoform, the human B cell line Ramos (IgM⁺ B lymphocytes, ATCC) stably expressing mα1.Fc$_L$-456C (SEQ ID NO:6) or mα1.Fc$_S$ (SEQ ID NO:7), designated as Ramos/mα1.Fc$_L$-456C and Ramos/mα1.Fc$_S$, respectively, were prepared. In brief, $5 \times 10^6$ Ramos cells were resuspended in 300 µl of serum-free RPMI 1640 medium (Invitrogen) containing 15 µg of constructed DNA and shocked at 230V/950 µF by Gene Pulser Xcell Electroporation Systems (Bio-Rad) subsequently. Cells were immediately transferred into complete RPMI medium (RPMI plus 10% FBS and penicillin/streptomycin). After growing for two days, cells were transferred into complete RPMI medium plus 1 mg/ml of G418 (Merck) for selecting stable transfectants. The stable cell clones expressing mα1.Fc$_L$-456C and mα1.Fc$_S$ were picked, respectively, by flow cytometric analyses with FITC-labeled goat anti-human IgA antibodies and were maintained in complete RPMI medium plus 0.5 mg/ml of G418.

Figure 5:
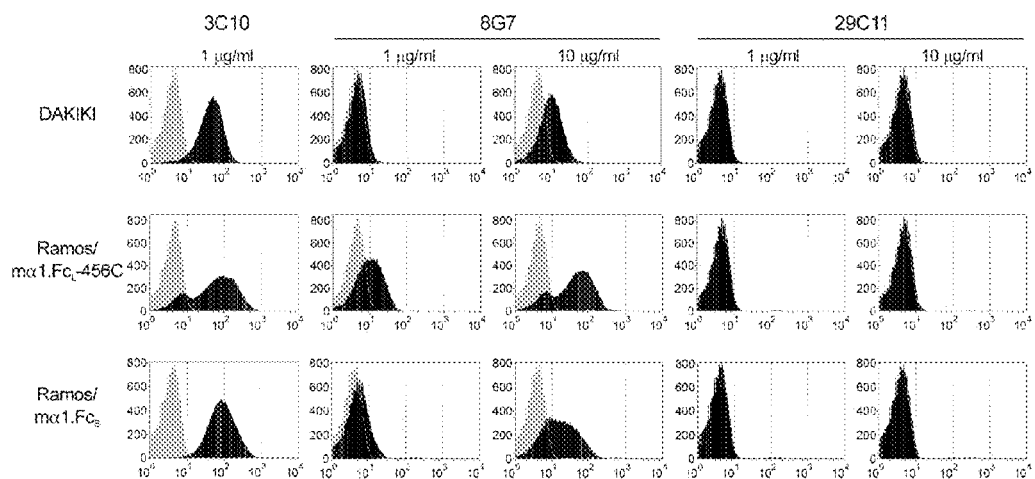
FIG. 5 shows staining profiles of anti-migis-α mAbs on DAKIKI cells and mα1.Fc-expressing Ramos transfectomas. The gray profiles are negative control mAbs of the same IgG isotypes.

For flow cytometric assays in the examples, 3C10 was used as a positive control of detecting mIgA expression and a mouse anti-human mIgE mAb 4B12 (Igγ1, κ) was served as a negative control. To perform the cell staining, $10^6$ cells were washed and incubated with mAbs in 100 µl of staining buffers on ice for 30 min. Cells were subsequently washed with staining buffers and incubated with FITC-labeled rabbit F(ab')$_2$ anti-mouse IgG antibodies (Invitrogen) 1:400 diluted in 100 µl staining buffers on ice for 30 min. After washing, cells were resuspended in 400 µl of staining buffers and subjected to flow cytometric analyses in a FACSCanto II (BD Biosciences). FIG. 5 shows that 8G7 binds to DAKIKI cells and Ramos transfectomas in a dose-dependent fashion and fluorescence intensities are significantly increased at the high concentration (10 µg/ml) at which concentration 29C11 binds to the cells poorly. At the low concentrations (1 µg/ml) staining signals of 29C11 towards these three mIgA-expressing B cells are undetectable. The increment of the mean fluorescence intensity (MFI) of 8G7 against DAKIKI {(MFI [high concentration]−MFI [background])−(MFI [low concentration]−MFI [background])} is 12.51 folds higher than that of 29C11. At the low concentration (1 µg/ml) the MFI of 8G7 against Ramos/mα1.Fc$_L$-456S and Ramos/mα1.Fc$_S$ over backgrounds {(MFI$_{8G7}$−MFI$_{background}$)/(MFI$_{29C11}$−MFI$_{background}$)} are 13.49 and 10.37 folds higher than those of 29l1, respectively.

Figure 6:
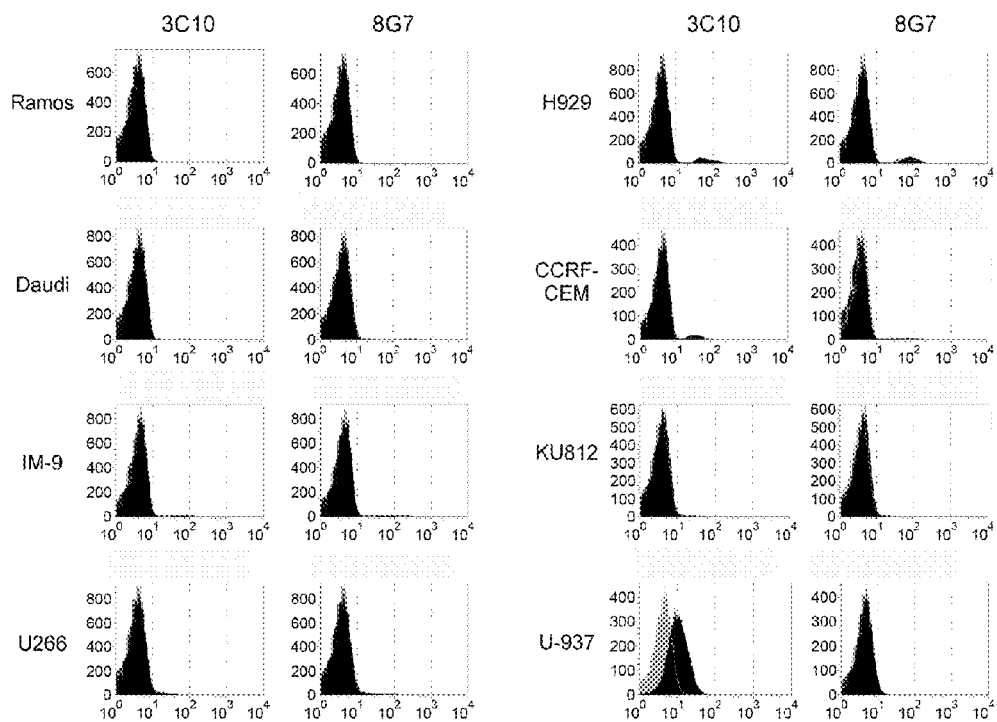
FIG. 6 shows the absence of reactivity of 8G7 mAb with 8 non-mIgA-expressing cell lines.

Several of non-mIgA-expressing cell lines, which were Ramos, Daudi (IgM⁺ B lymphocytes, ATCC), IM-9 (IgG⁺ B lymphocytes, ATCC), U266 (IgE⁺ B lymphocytes, ATCC), H929 (IgA⁺ B lymphocytes, ATCC), CCRF-CEM (T lymphocytes, ATCC), KU812 (Basophils, ATCC), and U-937 (Monocytes, ATCC), were examined for the reactivity by 8G7 (FIG. 6). Results show that 8G7 has no reactivity to surface molecules on these cell lines.

Figure 7:
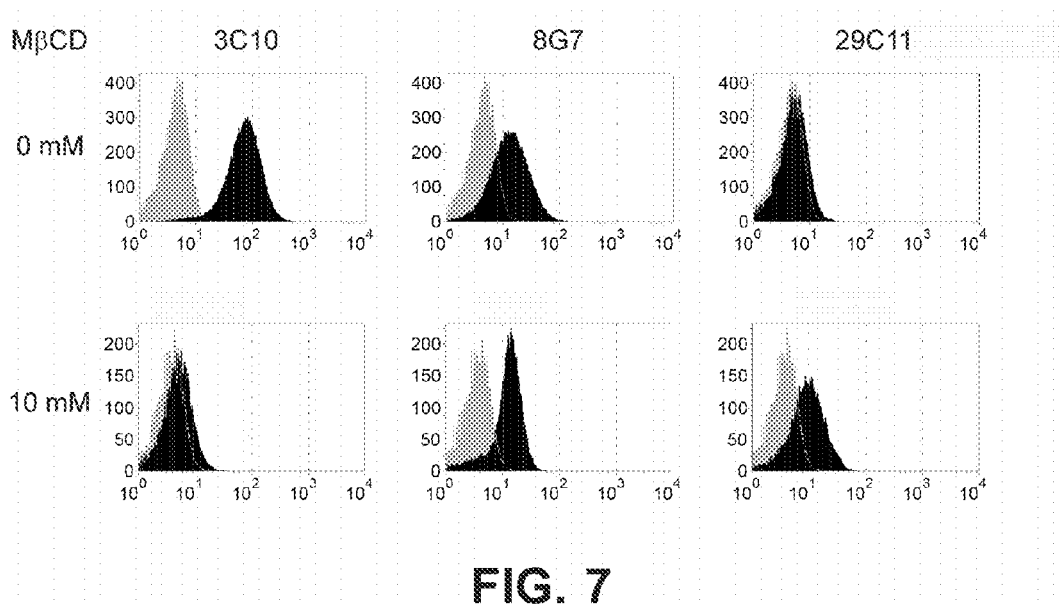
FIG. 7 shows the reactivity of anti-migis-α mAbs toward DAKIKI cells with or without MβCD treatments.

Since mIgA in associated with Igα/Igβ hetero dimers on B cell surfaces form B cell receptor complexes which can interact with lipid rafts, some of migis-α segments may be buried within the complexes. To study the hindrance of anti-migis-α mAbs reacting to mIgA on B cells, a cholesterol-extracting chemical methyl-β-cyclodextrin (MβCD, Sigma-Aldrich) was used to disrupt the integrity of mIgA receptor complexes. DAKIKI cells washed with pre-warmed RPMI medium twice were resuspended in 10 mM MβCD in RPMI medium ($5 \times 10^6$ cells/ml) and incubated at 37° C. with occasional agitation for 30 min. Cells were subsequently washed with staining buffers twice and subjected to cell staining for flow cytometric analyses. MAbs at 10 µg/ml were used for staining and 1:400 diluted FITC-labeled rabbit F(ab')$_2$ anti-mouse IgG antibodies were used for detection. After MβCD treatment, 29C11 shows an increased signal of binding to DAKIKI cells, whereas the fluorescence intensity of 3C10 decreased by more than ten times (FIG. 7). In the same antibody concentration 8G7 can bind to MβCD treated DAKIKI cells better than 3C10 and 29C11. Results in this example show that 8G7 is capable of binding to mIgA in its native form on B cell surfaces and 29C11 binds to mIgA only when lipid rafts are disrupted.

Example 5

Figure 8:
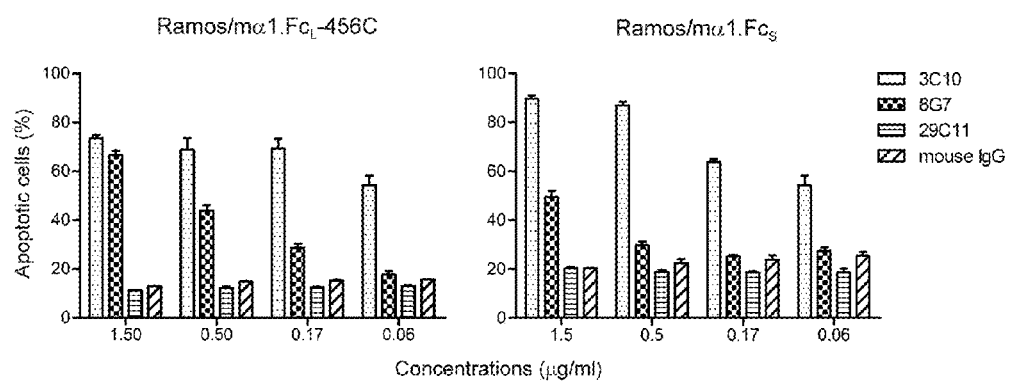
FIG. 8 shows results indicating that 3C10 and 8G7 can induce apoptosis in two mα1.Fc-expressing Ramos transfectomas, whereas 29C11 fails to do so.

Induction of Apoptosis by Anti-Migis-α mAb 8G7 in mIgA-Expressing B Transfectoma Cells To test whether cross-linking of mIgA receptor complexes could induce apoptotic signals, Ramos transfectomas, Ramos/mα1.Fc$_L$-456C and Ramos/mα1.Fc$_S$, respectively, were used for antibody treatment. In 96-well plates $10^5$ cells were seeded in 200 µl of completed RPMI 1640 medium in triplicate for each condition. Serial dilutions of mAb were added into wells and incubated at 37° C. for 1 hr. Goat F(ab')$_2$ anti-mouse IgG (Jackson ImmunoResearch) used for cross-linking were added into wells to a final concentration of 10 µg/ml and cells were cultured at 37° C. for 24 hr. Treat cells were then transferred into 5 ml polystyrene tubes and washed with PBS twice. To detect apoptosis, cells were stained with 2 µg of propidium iodide (PI, Sigma-Aldrich) and 1 µl of Annexin V-FITC (Biovision) in 100 µl of binding buffers [10 mM Hepes/NaOH (pH 7.4), 140 mM NaCl, 2.5 mM CaCl$_2$]. After incubation at room temperature for 20 min, 400 µl of binding buffers were added into tubes and cells were subsequently subjected to flow cytometric analyses. Apoptotic cells are defined as annexin V⁺/PI⁻ plus annexin V⁺/PI⁺. FIG. 8 shows that 3C10 and 8G7 in maximal concentrations (1.5 µg/ml) induce 73.67% and 66.68% of apoptosis in Ramos/mα1.Fc$_L$-456C, respectively. In the same concentrations 3C10 and 8G7 can induce 89.70% and 49.45% of apoptosis in Ramos/mα1.Fc$_S$ cells, respectively (FIG. 8). Within this concentration range 29C11 does not induce any significant apoptotic effect in these two Ramos transfectomas with comparing to results of mouse IgG controls. Comparing the efficiency of inducing apoptosis with these two transfectomas, 8G7 induces apoptosis stronger on Ramos/mα1.Fc$_L$-456C than on Ramos/mα1.Fc$_S$.

Example 6

Triggering of Antibody-Dependent Cellular Cytotoxicity (ADCC) of Human PBMCs with Mouse/Human Chimeric Anti-Migis-α mAb c8G7

ADCC is one of effective mechanisms of antibodies to recruit Fcγ receptor-bearing effector cells, such as natural killer (NK) cells and macrophages, to destroy the target cells which are coated with antibodies. In this example two human mIgA1 transfectomas, Ramos/mα1.Fc$_L$-456C and Ramos/mα1.Fc$_S$, respectively, were used as target cells and human PBMCs isolated from white blood cell concentrates obtained from the blood bank (Taipei, Taiwan) were served as effector cells. The manipulation of human blood samples was under the approval of Institutional Research Board on Biomedical Science Research (Academia Sinica, Taiwan). Mouse/human chimeric mAbs were prepared by replacing mouse γ and κ constant regions with respective human counterparts (γ1 and κ) by gene engineering and expressed with FreeStyle™ 293 Expression System. Chimeric 8G7 and 29C11 were denoted as c8G7 and c29C11, respectively. The mouse/human chimeric mAb cBAT123 which reacts with gp120 proteins was used as a negative control in the experiment.

To prepare PBMCs, white blood cell concentrates (50 ml) were mixed with 50 ml of Hank's Balanced Salt Solution (HBSS, Invitrogen) and 20 ml of diluted concentrates were carefully loaded onto 15 ml of Ficoll-Hypaque Plus solutions (GE healthcare) in a 50-ml canonical tube. Four tubes for 100 ml of total diluted concentrates were centrifuged at 300×g for 40 min to fractionate PBMCs from residual red blood cells in concentrates. PBMC layers were withdrawn and washed with 50 ml of HBSS three times. The number of PBMCs was calculated with the trypan blue exclusion method and PBMCs with required cell numbers were resuspended in complete RPMI medium at $5 \times 10^6$ cells/ml for following use. The remaining PBMCs were stored in FBS with 10% dimethyl sulfoxide in liquid nitrogen. To use preserved PBMCs as effector cells, PBMCs were thawed and cultured in complete RPMI medium for 24 hours before performing ADCC assays.

To label target cells with carboxyfluorescein succinimidyl ester (CFSE, Invitrogen), $1 \times 10^6$ transfectoma cells were washed with 10 ml of warm 0.1% BSA/PBS once and resuspended in 1 ml of warm 0.1% BSA/PBS with 1 µM CFSE followed by incubating at 37° C. for 10 min. The ice-cold completed RPMI medium (3 ml) were added into labelled cells and incubated on ice for 5 min. Cells were then spinned down to remove the medium and washed with 1 ml of ice-cold completed RPMI medium twice. Labelled cells were then resuspended in warm complete RPMI medium at $2 \times 10^5$ cells/ml for following assays. To test ADCC activity, $2 \times 10^4$ labelled target cells (100 µl) were transferred into each well in a round bottom 96-well culture plate. Chimeric antibodies (5 µl) with different concentrations were added into wells and incubated at 37° C. for 30 min followed by mixing with $5 \times 10^5$ PBMCs (100 µl). Cell mixtures were then cultured at 37° C. for 16-20 hr. In this example PBMCs of four donors were tested individually and experiments for each antibody concentration were triplicated. Before subjecting cells for flow cytometric analysis in a FACSCanto II, 0.25 µg of 7-aminoactinomycin D (7-AAD) were added into each well and incubated at room temperature for 15 min. Living target cells were defined as CFSE$^+$/7-AAD$^-$. Percentages of target cell lysis (% of ADCC) were calculated as the equation below.

% of target cell lysis={([% of living target cells]$_{no\ mAb\ treated}$−[% of living target cells]$_{mAb\ treated}$)/[% of living target cells]$_{no\ mAb\ treated}$}*100

Figure 9:
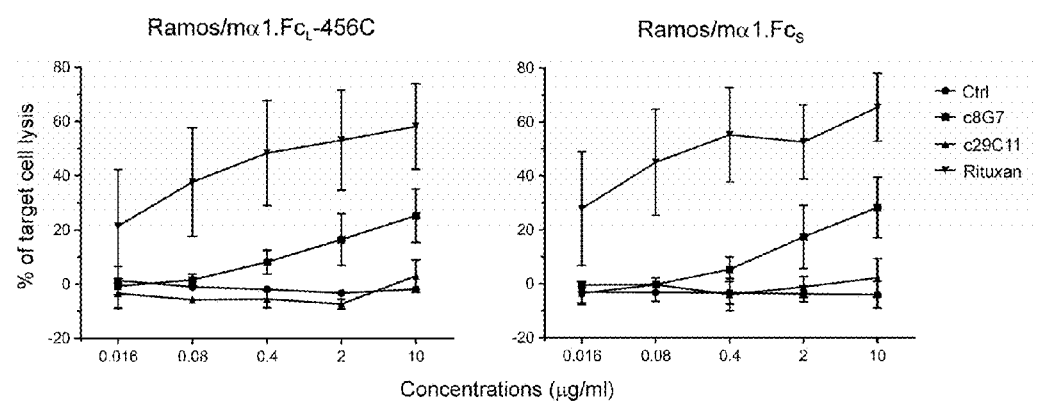
FIG. 9 shows results indicating that c8G7, but not c29C11, can induce significant ADCC in a dose-dependent manner. N=4

Results show that Rituxan and c8G7 display a dose-dependent ADCC to these two target cells (FIG. 9). c8G7 at the concentration of 10 µg/ml induces 25.23% and 28.30% of ADCC for Ramos/mα1.Fc$_L$-456C and Ramos/mα1.Fc$_S$, respectively (FIG. 9). At the same concentration Rituxan induces 58.16% and 65.40% of cell lysis for Ramos/mα1.Fc$_L$-456C and Ramos/mα1.Fc$_S$, respectively. Within the range of antibody concentrations tested in this example, significant ADCC cannot be observed in c29C11 groups.

Example 7

Reduction of IgA Production by Human PBMCs Treated with Mouse/Human Chimeric Anti-Migis-α mAb c8G7 In Vitro PBMCs from 22 healthy donors were prepared with procedures described in the previous example. Cells were resuspended in complete IMDM (Invitrogen) at the concentration of $2 \times 10^6$/ml and 200 µl of cells were transferred into each well in a 96-well culture plate. Antibodies were then added into wells with the final concentration of 5 µg/ml. After culturing for 5 days, cells were spinned at 400×g for 5 min and the supernatants (150 µl for each well) were mixed with equal volumes of 1% BSA/PBS. IgA and IgM levels were quantitated with Human IgA and IgM ELISA kits (Bethyl Laboratories, Inc), respectively, and procedures described in the attached manual were followed. In this example the mouse/human chimeric antibody 4B12 which specifically reacted with human membrane-bound IgE was used as a control mAb, and experiments for each antibody-treating group were repeated three times. The data correlation between measurements was calculated by paired samples t-tests.

Figure 10A:
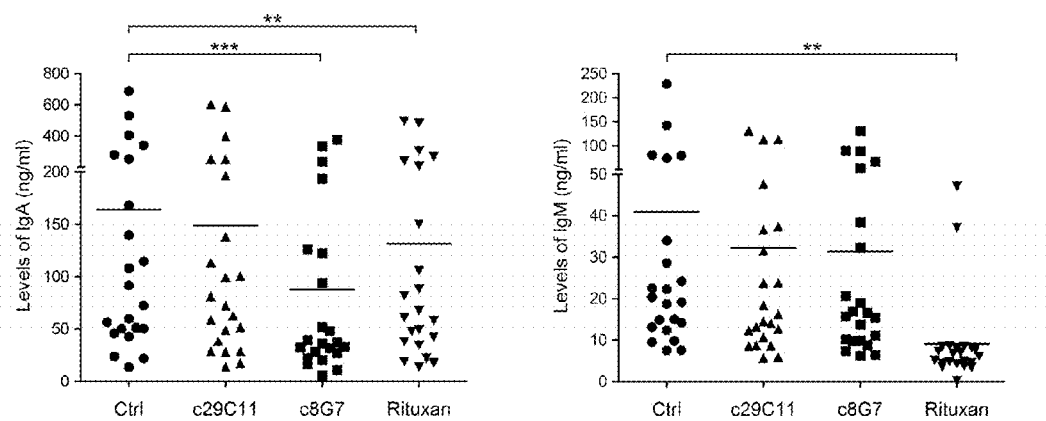
FIG. 10A-10B show measurements of IgA and IgM levels of antibody-treated human PBMCs from 22 donors in vitro. A)
Figure 10B:
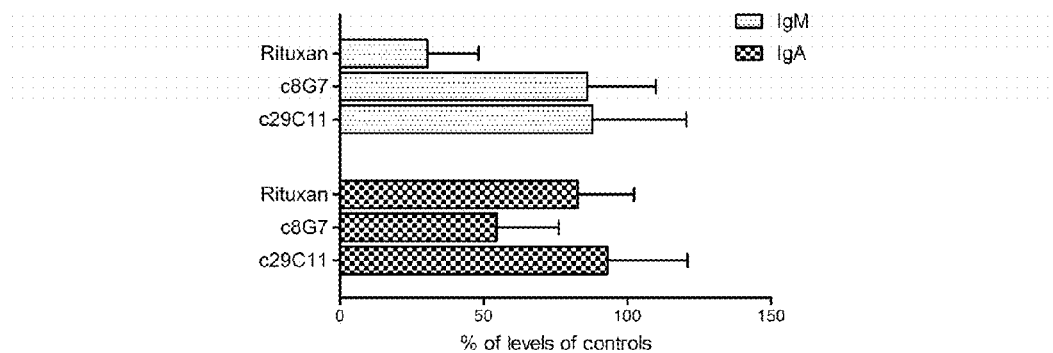

Results show that IgA levels are decreased in c8G7- and Rituxan-treated groups with high statistical significances by comparing with that in the control group (FIG. 10A). c29C11 at this treated concentration cannot reduce the IgA production (FIG. 10A). Although IgM levels in c29C11- and c8G7-treated groups are slightly lower than that in the control group, no statistical significance between each of them and the control group is observed (FIG. 10A). In constract, Rituxan can efficiently inhibit the production of IgM (FIG. 10A). FIG. 10B shows percentages of IgA and IgM levels of each group to the control group. In this treating condition, c8G7 and Rituxan decreases 50% and 20% of IgA levels of the control group, respectively (FIG. 10B). Only Rituxan can reduce the IgM level up to 40% of the control group with statistical significance (FIG. 10B).

Example 8

Growth Inhibition of mIgA-Expressing B Transfectoma Cells Transplanted into Mice Treated with the Anti-Migis-α mAb 8G7

Figure 11A:
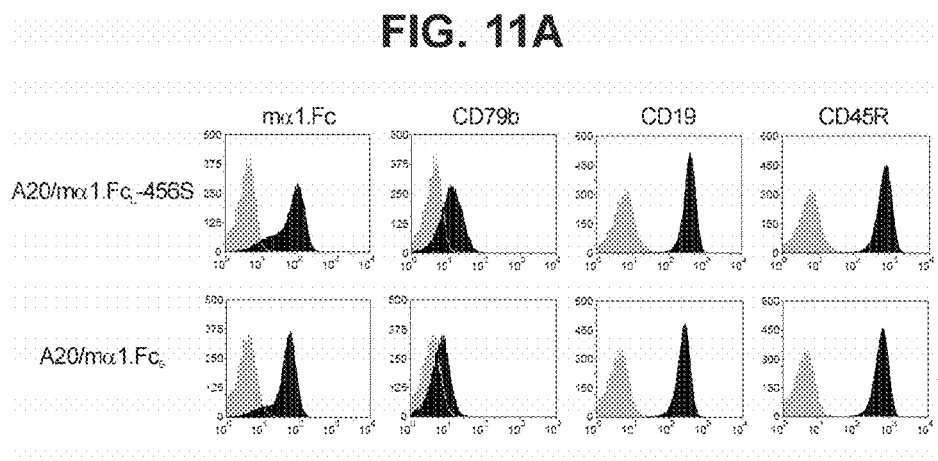
FIG. 11A-11B show the study of growth inhibition of mα1.Fc-expressing A20 transfectomas treated with anti-migis-α antibodies in vivo. A)

The mouse B cell line A20 (IgG$^+$ B lymphocytes, ATCC) stably expressing mα1.Fc$_L$-456S (SEQ ID NO:8) or mα1.Fc$_S$ (SEQ ID NO:7), designated as A20/mα1.Fc$_L$-456S and A20/mα1.Fc$_S$, respectively, were prepared with cell electroporation and drug selection procedures as same for preparing Ramos transfectomas in the previous example. Stable cell clones expressing mα1.Fc$_L$-456S and mα1.Fc$_S$ were picked, respectively, by flow cytometric analyses with FITC-labeled goat anti-human IgA antibodies (FIG. 11A) and were maintained in complete RPMI medium plus 0.5 mg/ml of G418. Mouse B cell markers CD19, CD45R, and CD79b of two transfectoma cells were also examined by flow cytometric assays with FITC-labeled rat anti-mouse CD19, PE-labeled rat anti-mouse CD45R, and FITC-labeled hamster anti-mouse CD79 (BD Biosciences), respectively (FIG. 11A).

To test growth inhibition of antibody-treated A20 transfectomas in vivo, cells were washed with Hank's Balanced Salt Solution (HBSS, Invitrogen) twice and resuspended in HBSS at $1 \times 10^8$ cells/ml. Cells were then mixed with Geltrex™ LDEV-Free Reduced Growth Factor Basement Membrane Matrix (Invitrogen) at the ratio 1:1 and carefully transferred into a syringe attached with a 22 gauge needle.

Figure 11B:
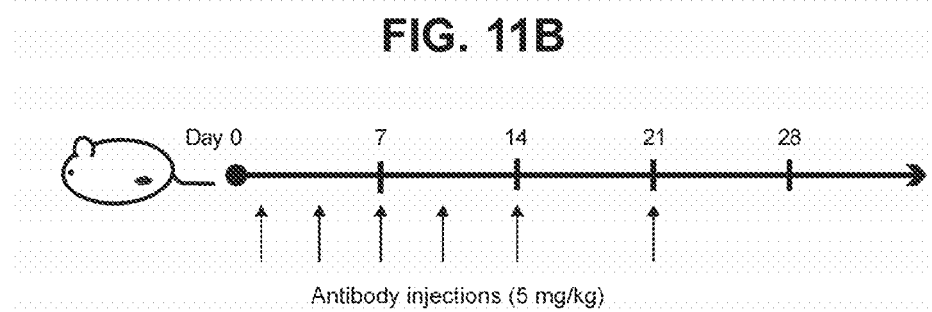

Cell mixtures (5×10⁶ cells/100 μl/site) were inoculated into the abdominal flank of C.B-17 scid mice with 6-8 weeks in age (National Laboratory Animal Center, Taiwan) subcutaneously. After the engraftment (day 0), mice received purified 29C11 or 8G7 at a dose of 5 mg/kg intravenously via the tail vein on days 1, 4, 7, 10, 14 and 21 (FIG. 11B). Purified mouse serum IgG (Sigma-Aldrich) was used for the control group. Five tumor-inoculated mice were tested for each antibody group. Tumor sizes were measured with a vernier caliper weekly and volumes were calculated by using the formula: ½×Length×Width. Mice were sacrificed when tumors reached the volume of 3000 mm³.

---

What is claimed is:

1. An anti-migis-α antibody or a fragment thereof specific for the migis-α of human ma chain that can bind to mIgA on B lymphocytes, thereby causing the lysis of mIgA-expressing B lymphocytes, and/or decreasing IgA production by IgA-secreting B lymphocytes, wherein the anti-migis-α antibody or a fragment thereof comprises the following complementary-determining regions (CDRs):
   (a) the CDR-H1 is residues 26-33 of SEQ ID NO:17,
   (b) the CDR-H2 is residues 51-57 of SEQ ID NO:17,
   (c) the CDR-H3 is residues 96-104 of SEQ ID NO:17,
   (d) the CDR-L1 is residues 27-32 of SEQ ID NO:18,
   (e) the CDR-L2 is residues 50-52 of SEQ ID NO:18,
   (f) the CDR-L3 is residues 89-97 of SEQ ID NO:18.

2. The anti-migis-α antibody or a fragment thereof according to claim 1, which comprises or is an F(ab)'2, an Fab, an Fv, or a single-chain Fv fragment of the anti-migis-α antibodies.

3. The anti-migis-α antibody or a fragment thereof according to claim 1, wherein the antibody or the fragment thereof comprises VH set forth in SEQ ID NO:17 and VL set forth in SEQ ID NO:18.

4. The anti-migis-α antibody or a fragment thereof according to claim 1, wherein the antibody or the fragment thereof is a chimeric, humanized, or human antibody or a fragment thereof.

5. A pharmaceutical composition comprising the anti-migis-α antibody or a fragment thereof according to claim 1 and a pharmaceutically acceptable carrier.

6. The pharmaceutical composition according to claim 5, wherein the pharmaceutical composition is used for treating a disease in a subject which can benefit from the elimination of mIgA-expressing cells or the reduction of IgA antibodies in the immune system.

7. The pharmaceutical composition according to claim 6, wherein the disease is selected from the group consisting of IgA lymphoctyes, IgA nephropathy (IgAN), Henoch-Schönlein purpura (HSP) and Celiac disease.

8. The pharmaceutical composition according to claim 5, wherein the anti-migis-α antibody or a fragment thereof comprises or is an F(ab)'2, an Fab, an Fv, or a single-chain Fv fragment of the anti-migis-α antibodies.

9. The pharmaceutical composition according to claim 5, wherein the anti-migis-α antibody or the fragment thereof comprises VH set forth in SEQ ID NO:17 and VL set forth in SEQ ID NO:18.

10. The pharmaceutical composition according to claim 5, wherein the anti-migis-α antibody or the fragment thereof is a chimeric, humanized, or human antibody or a fragment thereof.

11. A method for lysing mIgA-expressing B lymphocytes and reducing IgA production in a subject in vitro or in vivo comprising employing to the subject an antibody or a fragment thereof according to claim 1, thereby causing the lysis of mIgA-expressing B lymphocytes, and decreasing IgA production by IgA-secreting B lymphocytes.

12. A method for treating a disease in a subject, comprising administering to the subject an antibody or a fragment thereof according to claim 1, thereby lysing mIgA-expressing B lymphocytes and reducing IgA production in the immune system of the subject.

13. The method according to claim 12, wherein the disease is selected from the group consisting of IgA lymphoctyes, IgA nephropathy (IgAN), Henoch-Schönlein purpura (HSP) and Celiac disease.

14. The method according to claim 12, wherein the anti-migis-α antibody or the fragment thereof comprises VH set forth in SEQ ID NO:17 and VL set forth in SEQ ID NO:18.

* * * * *

SEQUENCE LISTING

```
<160> NUMBER OF SEQ ID NOS: 20

<210> SEQ ID NO 1
<211> LENGTH: 306
<212> TYPE: PRT
<213> ORGANISM: Artificial Sequence
<220> FEATURE:
<223> OTHER INFORMATION: Mouse/human chimeric migis-alpha L-containing
      protein

<400> SEQUENCE: 1

Asp Gly Gly Ser His His His His His His Ala Phe Lys Val Ala Ala
1               5                   10                  15

Trp Thr Leu Lys Ala Ala Ala Gly Pro Thr Pro Pro Pro Ile Thr
                20                  25                  30

Ile Pro Ser Cys Gln Pro Ser Leu Ser Leu Gln Arg Pro Ala Leu Glu
            35                  40                  45

Asp Leu Leu Leu Gly Ser Asp Ala Ser Ile Thr Cys Thr Leu Asn Gly
    50                  55                  60

Leu Arg Asn Pro Glu Gly Ala Ala Phe Thr Trp Glu Pro Ser Thr Gly
65                  70                  75                  80

Lys Asp Ala Val Gln Lys Lys Ala Ala Gln Asn Ser Cys Gly Cys Tyr
                85                  90                  95

Ser Val Ser Ser Val Leu Pro Gly Cys Ala Glu Arg Trp Asn Ser Gly
            100                 105                 110

Ala Ser Phe Lys Cys Thr Val Thr His Pro Glu Ser Gly Thr Leu Thr
        115                 120                 125

Gly Thr Ile Ala Lys Val Thr Val Asn Thr Phe Pro Pro Gln Val His
    130                 135                 140

Leu Leu Pro Pro Pro Ser Glu Glu Leu Ala Leu Asn Glu Leu Leu Ser
145                 150                 155                 160

Leu Thr Cys Leu Val Arg Ala Phe Asn Pro Lys Glu Val Leu Val Arg
                165                 170                 175

Trp Leu His Gly Asn Glu Glu Leu Ser Pro Glu Ser Tyr Leu Val Phe
            180                 185                 190

Glu Pro Leu Lys Glu Pro Gly Glu Gly Ala Thr Thr Tyr Leu Val Thr
        195                 200                 205

Ser Val Leu Arg Val Ser Ala Glu Thr Trp Lys Gln Gly Asp Gln Tyr
    210                 215                 220

Ser Cys Met Val Gly His Glu Ala Leu Pro Met Asn Phe Thr Gln Lys
225                 230                 235                 240

Thr Ile Asp Arg Leu Ala Gly Ser Cys Ser Val Ala Asp Trp Gln Met
                245                 250                 255

Pro Pro Pro Tyr Val Val Leu Asp Leu Pro Gln Glu Thr Leu Glu Glu
            260                 265                 270

Glu Thr Pro Gly Ala Asn Leu Glu Asp Lys Val Glu Glu Leu Leu Ser
        275                 280                 285

Lys Asn Tyr His Leu Glu Asn Glu Val Ala Arg Leu Lys Lys Leu Val
    290                 295                 300

Gly Glu
```

<210> SEQ ID NO 2
<211> LENGTH: 243
<212> TYPE: PRT
<213> ORGANISM: Homo sapiens
<220> FEATURE:
<223> OTHER INFORMATION: Human m-A1.Fc

<400> SEQUENCE: 2

```
Asp Gly Gly Ser His His His His His Gly Ser Val Pro Ser Thr
 1               5                  10                  15

Pro Pro Thr Pro Ser Pro Ser Thr Pro Pro Thr Pro Ser Pro Ser Cys
                20                  25                  30

Cys His Pro Arg Leu Ser Leu His Arg Pro Ala Leu Glu Asp Leu Leu
                35                  40                  45

Leu Gly Ser Glu Ala Asn Leu Thr Cys Thr Leu Thr Gly Leu Arg Asp
            50                  55                  60

Ala Ser Gly Val Thr Phe Thr Trp Thr Pro Ser Ser Gly Lys Ser Ala
65                  70                  75                  80

Val Gln Gly Pro Pro Glu Arg Asp Leu Cys Gly Cys Tyr Ser Val Ser
                85                  90                  95

Ser Val Leu Pro Gly Cys Ala Glu Pro Trp Asn His Gly Lys Thr Phe
                100                 105                 110

Thr Cys Thr Ala Ala Tyr Pro Glu Ser Lys Thr Pro Leu Thr Ala Thr
                115                 120                 125

Leu Ser Lys Ser Gly Asn Thr Phe Arg Pro Glu Val His Leu Leu Pro
            130                 135                 140

Pro Pro Ser Glu Glu Leu Ala Leu Asn Glu Leu Val Thr Leu Thr Cys
145                 150                 155                 160

Leu Ala Arg Gly Phe Ser Pro Lys Asp Val Leu Val Arg Trp Leu Gln
                165                 170                 175

Gly Ser Gln Glu Leu Pro Arg Glu Lys Tyr Leu Thr Trp Ala Ser Arg
                180                 185                 190

Gln Glu Pro Ser Gln Gly Thr Thr Thr Phe Ala Val Thr Ser Ile Leu
                195                 200                 205

Arg Val Ala Ala Glu Asp Trp Lys Lys Gly Asp Thr Phe Ser Cys Met
            210                 215                 220

Val Gly His Glu Ala Leu Pro Leu Ala Phe Thr Gln Lys Thr Ile Asp
225                 230                 235                 240

Arg Leu Ala
```

<210> SEQ ID NO 3
<211> LENGTH: 297
<212> TYPE: PRT
<213> ORGANISM: Homo sapiens
<220> FEATURE:
<223> OTHER INFORMATION: Human m-A1.FcS-LZ

<400> SEQUENCE: 3

```
Asp Gly Gly Ser His His His His His Gly Ser Val Pro Ser Thr
 1               5                  10                  15

Pro Pro Thr Pro Ser Pro Ser Thr Pro Pro Thr Pro Ser Pro Ser Cys
                20                  25                  30

Cys His Pro Arg Leu Ser Leu His Arg Pro Ala Leu Glu Asp Leu Leu
                35                  40                  45

Leu Gly Ser Glu Ala Asn Leu Thr Cys Thr Leu Thr Gly Leu Arg Asp
```

```
            50                  55                  60
Ala Ser Gly Val Thr Phe Thr Trp Thr Pro Ser Ser Gly Lys Ser Ala
 65                  70                  75                  80

Val Gln Gly Pro Pro Glu Arg Asp Leu Cys Gly Cys Tyr Ser Val Ser
                     85                  90                  95

Ser Val Leu Pro Gly Cys Ala Glu Pro Trp Asn His Gly Lys Thr Phe
                    100                 105                 110

Thr Cys Thr Ala Ala Tyr Pro Glu Ser Lys Thr Pro Leu Thr Ala Thr
                115                 120                 125

Leu Ser Lys Ser Gly Asn Thr Phe Arg Pro Glu Val His Leu Leu Pro
            130                 135                 140

Pro Pro Ser Glu Glu Leu Ala Leu Asn Glu Leu Val Thr Leu Thr Cys
145                 150                 155                 160

Leu Ala Arg Gly Phe Ser Pro Lys Asp Val Leu Val Arg Trp Leu Gln
                165                 170                 175

Gly Ser Gln Glu Leu Pro Arg Glu Lys Tyr Leu Thr Trp Ala Ser Arg
            180                 185                 190

Gln Glu Pro Ser Gln Gly Thr Thr Thr Phe Ala Val Thr Ser Ile Leu
        195                 200                 205

Arg Val Ala Ala Glu Asp Trp Lys Lys Gly Asp Thr Phe Ser Cys Met
210                 215                 220

Val Gly His Glu Ala Leu Pro Leu Ala Phe Thr Gln Lys Thr Ile Asp
225                 230                 235                 240

Arg Leu Ala Asp Trp Gln Met Pro Pro Tyr Val Val Leu Asp Leu
                245                 250                 255

Pro Gln Glu Thr Leu Glu Glu Glu Thr Pro Gly Ala Asn Leu Glu Asp
                260                 265                 270

Lys Val Glu Glu Leu Leu Ser Lys Asn Tyr His Leu Glu Asn Glu Val
                275                 280                 285

Ala Arg Leu Lys Lys Leu Val Gly Glu
                290                 295

<210> SEQ ID NO 4
<211> LENGTH: 303
<212> TYPE: PRT
<213> ORGANISM: Homo sapiens
<220> FEATURE:
<223> OTHER INFORMATION: Human m-A1.FcL-456S-LZ

<400> SEQUENCE: 4

Asp Gly Gly Ser His His His His His Gly Ser Val Pro Ser Thr
 1               5                  10                  15

Pro Pro Thr Pro Ser Pro Ser Thr Pro Pro Thr Pro Ser Pro Ser Cys
                 20                  25                  30

Cys His Pro Arg Leu Ser Leu His Arg Pro Ala Leu Glu Asp Leu Leu
             35                  40                  45

Leu Gly Ser Glu Ala Asn Leu Thr Cys Thr Leu Thr Gly Leu Arg Asp
         50                  55                  60

Ala Ser Gly Val Thr Phe Thr Trp Thr Pro Ser Ser Gly Lys Ser Ala
 65                  70                  75                  80

Val Gln Gly Pro Pro Glu Arg Asp Leu Cys Gly Cys Tyr Ser Val Ser
                     85                  90                  95

Ser Val Leu Pro Gly Cys Ala Glu Pro Trp Asn His Gly Lys Thr Phe
                    100                 105                 110

Thr Cys Thr Ala Ala Tyr Pro Glu Ser Lys Thr Pro Leu Thr Ala Thr
```

```
            115                 120                 125
Leu Ser Lys Ser Gly Asn Thr Phe Arg Pro Glu Val His Leu Leu Pro
    130                 135                 140
Pro Pro Ser Glu Glu Leu Ala Leu Asn Glu Leu Val Thr Leu Thr Cys
145                 150                 155                 160
Leu Ala Arg Gly Phe Ser Pro Lys Asp Val Leu Val Arg Trp Leu Gln
                165                 170                 175
Gly Ser Gln Glu Leu Pro Arg Glu Lys Tyr Leu Thr Trp Ala Ser Arg
            180                 185                 190
Gln Glu Pro Ser Gln Gly Thr Thr Thr Phe Ala Val Thr Ser Ile Leu
        195                 200                 205
Arg Val Ala Ala Glu Asp Trp Lys Lys Gly Asp Thr Phe Ser Cys Met
    210                 215                 220
Val Gly His Glu Ala Leu Pro Leu Ala Phe Thr Gln Lys Thr Ile Asp
225                 230                 235                 240
Arg Leu Ala Gly Ser Cys Ser Val Ala Asp Trp Gln Met Pro Pro Pro
                245                 250                 255
Tyr Val Val Leu Asp Leu Pro Gln Glu Thr Leu Glu Glu Glu Thr Pro
            260                 265                 270
Gly Ala Asn Leu Glu Asp Lys Val Glu Glu Leu Leu Ser Lys Asn Tyr
        275                 280                 285
His Leu Glu Asn Glu Val Ala Arg Leu Lys Lys Leu Val Gly Glu
    290                 295                 300
```

<210> SEQ ID NO 5
<211> LENGTH: 303
<212> TYPE: PRT
<213> ORGANISM: Homo sapiens
<220> FEATURE:
<223> OTHER INFORMATION: Human m-A1.FcL-456C-LZ

<400> SEQUENCE: 5

```
Asp Gly Gly Ser His His His His His Gly Ser Val Pro Ser Thr
1               5                   10                  15
Pro Pro Thr Pro Ser Pro Ser Thr Pro Pro Thr Pro Ser Pro Ser Cys
            20                  25                  30
Cys His Pro Arg Leu Ser Leu His Arg Pro Ala Leu Glu Asp Leu Leu
        35                  40                  45
Leu Gly Ser Glu Ala Asn Leu Thr Cys Thr Leu Thr Gly Leu Arg Asp
    50                  55                  60
Ala Ser Gly Val Thr Phe Thr Trp Thr Pro Ser Ser Gly Lys Ser Ala
65                  70                  75                  80
Val Gln Gly Pro Pro Glu Arg Asp Leu Cys Gly Cys Tyr Ser Val Ser
                85                  90                  95
Ser Val Leu Pro Gly Cys Ala Glu Pro Trp Asn His Gly Lys Thr Phe
            100                 105                 110
Thr Cys Thr Ala Ala Tyr Pro Glu Ser Lys Thr Pro Leu Thr Ala Thr
        115                 120                 125
Leu Ser Lys Ser Gly Asn Thr Phe Arg Pro Glu Val His Leu Leu Pro
    130                 135                 140
Pro Pro Ser Glu Glu Leu Ala Leu Asn Glu Leu Val Thr Leu Thr Cys
145                 150                 155                 160
Leu Ala Arg Gly Phe Ser Pro Lys Asp Val Leu Val Arg Trp Leu Gln
                165                 170                 175
Gly Ser Gln Glu Leu Pro Arg Glu Lys Tyr Leu Thr Trp Ala Ser Arg
```

-continued

```
            180                 185                 190
Gln Glu Pro Ser Gln Gly Thr Thr Thr Phe Ala Val Thr Ser Ile Leu
            195                 200                 205
Arg Val Ala Ala Glu Asp Trp Lys Lys Gly Asp Thr Phe Ser Cys Met
        210                 215                 220
Val Gly His Glu Ala Leu Pro Leu Ala Phe Thr Gln Lys Thr Ile Asp
225                 230                 235                 240
Arg Leu Ala Gly Ser Cys Cys Val Ala Asp Trp Gln Met Pro Pro Pro
                245                 250                 255
Tyr Val Leu Asp Leu Pro Gln Glu Thr Leu Glu Glu Thr Pro
                260                 265                 270
Gly Ala Asn Leu Glu Asp Lys Val Glu Glu Leu Leu Ser Lys Asn Tyr
            275                 280                 285
His Leu Glu Asn Glu Val Ala Arg Leu Lys Lys Leu Val Gly Glu
        290                 295                 300
```

<210> SEQ ID NO 6
<211> LENGTH: 314
<212> TYPE: PRT
<213> ORGANISM: Homo sapiens
<220> FEATURE:
<223> OTHER INFORMATION: Human m-A1.FcL-456C

<400> SEQUENCE: 6

```
Asp Gly Gly Ser His His His His Gly Ser Val Pro Ser Thr
1               5                   10                  15
Pro Pro Thr Pro Ser Pro Ser Thr Pro Pro Thr Pro Ser Pro Ser Cys
                20                  25                  30
Cys His Pro Arg Leu Ser Leu His Arg Pro Ala Leu Glu Asp Leu Leu
            35                  40                  45
Leu Gly Ser Glu Ala Asn Leu Thr Cys Thr Leu Thr Gly Leu Arg Asp
        50                  55                  60
Ala Ser Gly Val Thr Phe Thr Trp Thr Pro Ser Ser Gly Lys Ser Ala
65                  70                  75                  80
Val Gln Gly Pro Pro Glu Arg Asp Leu Cys Gly Cys Tyr Ser Val Ser
                85                  90                  95
Ser Val Leu Pro Gly Cys Ala Glu Pro Trp Asn His Gly Lys Thr Phe
                100                 105                 110
Thr Cys Thr Ala Ala Tyr Pro Glu Ser Lys Thr Pro Leu Thr Ala Thr
            115                 120                 125
Leu Ser Lys Ser Gly Asn Thr Phe Arg Pro Glu Val His Leu Leu Pro
        130                 135                 140
Pro Pro Ser Glu Glu Leu Ala Leu Asn Glu Leu Val Thr Leu Thr Cys
145                 150                 155                 160
Leu Ala Arg Gly Phe Ser Pro Lys Asp Val Leu Val Arg Trp Leu Gln
                165                 170                 175
Gly Ser Gln Glu Leu Pro Arg Glu Lys Tyr Leu Thr Trp Ala Ser Arg
            180                 185                 190
Gln Glu Pro Ser Gln Gly Thr Thr Thr Phe Ala Val Thr Ser Ile Leu
            195                 200                 205
Arg Val Ala Ala Glu Asp Trp Lys Lys Gly Asp Thr Phe Ser Cys Met
        210                 215                 220
Val Gly His Glu Ala Leu Pro Leu Ala Phe Thr Gln Lys Thr Ile Asp
225                 230                 235                 240
Arg Leu Ala Gly Ser Cys Cys Val Ala Asp Trp Gln Met Pro Pro Pro
```

```
              245                 250                 255
Tyr Val Val Leu Asp Leu Pro Gln Glu Thr Leu Glu Glu Thr Pro
            260                 265                 270
Gly Ala Asn Leu Trp Pro Thr Thr Ile Thr Phe Leu Thr Leu Phe Leu
            275                 280                 285
Leu Ser Leu Phe Tyr Ser Thr Ala Leu Thr Val Thr Ser Val Arg Gly
            290                 295                 300
Pro Ser Gly Asn Arg Glu Gly Pro Gln Tyr
305                 310

<210> SEQ ID NO 7
<211> LENGTH: 308
<212> TYPE: PRT
<213> ORGANISM: Homo sapiens
<220> FEATURE:
<223> OTHER INFORMATION: Human m-A1.FcS

<400> SEQUENCE: 7

Asp Gly Gly Ser His His His His His Gly Ser Val Pro Ser Thr
1               5                   10                  15
Pro Pro Thr Pro Ser Pro Ser Thr Pro Pro Thr Pro Ser Pro Ser Cys
            20                  25                  30
Cys His Pro Arg Leu Ser Leu His Arg Pro Ala Leu Glu Asp Leu Leu
            35                  40                  45
Leu Gly Ser Glu Ala Asn Leu Thr Cys Thr Leu Thr Gly Leu Arg Asp
            50                  55                  60
Ala Ser Gly Val Thr Phe Thr Trp Thr Pro Ser Ser Gly Lys Ser Ala
65                  70                  75                  80
Val Gln Gly Pro Pro Glu Arg Asp Leu Cys Gly Cys Tyr Ser Val Ser
            85                  90                  95
Ser Val Leu Pro Gly Cys Ala Glu Pro Trp Asn His Gly Lys Thr Phe
            100                 105                 110
Thr Cys Thr Ala Ala Tyr Pro Glu Ser Lys Thr Pro Leu Thr Ala Thr
            115                 120                 125
Leu Ser Lys Ser Gly Asn Thr Phe Arg Pro Glu Val His Leu Leu Pro
            130                 135                 140
Pro Pro Ser Glu Glu Leu Ala Leu Asn Glu Leu Val Thr Leu Thr Cys
145                 150                 155                 160
Leu Ala Arg Gly Phe Ser Pro Lys Asp Val Leu Val Arg Trp Leu Gln
            165                 170                 175
Gly Ser Gln Glu Leu Pro Arg Glu Lys Tyr Leu Thr Trp Ala Ser Arg
            180                 185                 190
Gln Glu Pro Ser Gln Gly Thr Thr Thr Phe Ala Val Thr Ser Ile Leu
            195                 200                 205
Arg Val Ala Ala Glu Asp Trp Lys Lys Gly Asp Thr Phe Ser Cys Met
210                 215                 220
Val Gly His Glu Ala Leu Pro Leu Ala Phe Thr Gln Lys Thr Ile Asp
225                 230                 235                 240
Arg Leu Ala Asp Trp Gln Met Pro Pro Tyr Val Val Leu Asp Leu
            245                 250                 255
Pro Gln Glu Thr Leu Glu Glu Thr Pro Gly Ala Asn Leu Trp Pro
            260                 265                 270
Thr Thr Ile Thr Phe Leu Thr Leu Phe Leu Ser Leu Phe Tyr Ser
            275                 280                 285
Thr Ala Leu Thr Val Thr Ser Val Arg Gly Pro Ser Gly Asn Arg Glu
```

```
                290                 295                 300

Gly Pro Gln Tyr
305

<210> SEQ ID NO 8
<211> LENGTH: 314
<212> TYPE: PRT
<213> ORGANISM: Homo sapiens
<220> FEATURE:
<223> OTHER INFORMATION: Human m-A1.FcL-456S

<400> SEQUENCE: 8

Asp Gly Gly Ser His His His His His Gly Ser Val Pro Ser Thr
1               5                   10                  15

Pro Pro Thr Pro Ser Pro Ser Thr Pro Pro Thr Pro Ser Pro Ser Cys
                20                  25                  30

Cys His Pro Arg Leu Ser Leu His Arg Pro Ala Leu Glu Asp Leu Leu
                35                  40                  45

Leu Gly Ser Glu Ala Asn Leu Thr Cys Thr Leu Thr Gly Leu Arg Asp
    50                  55                  60

Ala Ser Gly Val Thr Phe Thr Trp Thr Pro Ser Ser Gly Lys Ser Ala
65                  70                  75                  80

Val Gln Gly Pro Pro Glu Arg Asp Leu Cys Gly Cys Tyr Ser Val Ser
                85                  90                  95

Ser Val Leu Pro Gly Cys Ala Glu Pro Trp Asn His Gly Lys Thr Phe
                100                 105                 110

Thr Cys Thr Ala Ala Tyr Pro Glu Ser Lys Thr Pro Leu Thr Ala Thr
            115                 120                 125

Leu Ser Lys Ser Gly Asn Thr Phe Arg Pro Glu Val His Leu Leu Pro
    130                 135                 140

Pro Pro Ser Glu Glu Leu Ala Leu Asn Glu Leu Val Thr Leu Thr Cys
145                 150                 155                 160

Leu Ala Arg Gly Phe Ser Pro Lys Asp Val Leu Val Arg Trp Leu Gln
                165                 170                 175

Gly Ser Gln Glu Leu Pro Arg Glu Lys Tyr Leu Thr Trp Ala Ser Arg
                180                 185                 190

Gln Glu Pro Ser Gln Gly Thr Thr Thr Phe Ala Val Thr Ser Ile Leu
            195                 200                 205

Arg Val Ala Ala Glu Asp Trp Lys Lys Gly Asp Thr Phe Ser Cys Met
    210                 215                 220

Val Gly His Glu Ala Leu Pro Leu Ala Phe Thr Gln Lys Thr Ile Asp
225                 230                 235                 240

Arg Leu Ala Gly Ser Cys Ser Val Ala Asp Trp Gln Met Pro Pro Pro
                245                 250                 255

Tyr Val Val Leu Asp Leu Pro Gln Glu Thr Leu Glu Glu Glu Thr Pro
                260                 265                 270

Gly Ala Asn Leu Trp Pro Thr Thr Ile Thr Phe Leu Thr Leu Phe Leu
            275                 280                 285

Leu Ser Leu Phe Tyr Ser Thr Ala Leu Thr Val Thr Ser Val Arg Gly
    290                 295                 300

Pro Ser Gly Asn Arg Glu Gly Pro Gln Tyr
305                 310

<210> SEQ ID NO 9
<211> LENGTH: 36
<212> TYPE: PRT
```

```
<213> ORGANISM: Artificial Sequence
<220> FEATURE:
<223> OTHER INFORMATION: Synthetic peptide maFL

<400> SEQUENCE: 9

Asp Arg Leu Ala Gly Ser Cys Ser Val Ala Asp Trp Gln Met Pro Pro
1               5                   10                  15

Pro Tyr Val Val Leu Asp Leu Pro Gln Glu Thr Leu Glu Glu Glu Thr
                20                  25                  30

Pro Gly Ala Asn
        35

<210> SEQ ID NO 10
<211> LENGTH: 18
<212> TYPE: PRT
<213> ORGANISM: Artificial Sequence
<220> FEATURE:
<223> OTHER INFORMATION: Synthetic peptide maFa

<400> SEQUENCE: 10

Gly Ser Cys Ser Val Ala Asp Trp Gln Met Pro Pro Pro Tyr Val Val
1               5                   10                  15

Leu Asp

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide maFb

<400> SEQUENCE: 11

Gln Met Pro Pro Pro Tyr Val Val Leu Asp Leu Pro Gln Glu Thr Leu
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide maFc

<400> SEQUENCE: 12

Leu Asp Leu Pro Gln Glu Thr Leu Glu Glu Glu Thr Pro Gly Ala Asn
1               5                   10                  15

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide maF1-2

<400> SEQUENCE: 13

Gly Ser Cys Ser Val Ala Asp Trp Gln Met Pro Pro
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide maF1-3

<400> SEQUENCE: 14
```

```
Cys Ser Val Ala Asp Trp Gln Met Pro Pro Pro Tyr
1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: Synthetic peptide maF2

<400> SEQUENCE: 15

```
Val Ala Asp Trp Gln Met Pro Pro Pro Tyr Val Val
1               5                   10
```

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide maF2-1

<400> SEQUENCE: 16

```
Asp Trp Gln Met Pro Pro Pro Tyr Val Val Leu Asp
1               5                   10
```

<210> SEQ ID NO 17
<211> LENGTH: 115
<212> TYPE: PRT
<213> ORGANISM: Mus musculus
<220> FEATURE:
<223> OTHER INFORMATION: Variable region of mouse 8G7 heavy chain

<400> SEQUENCE: 17

```
Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Asn Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ser Thr Tyr Tyr Asn Pro Ser Leu Lys
    50                  55                  60

Ser Arg Ile Phe Ile Thr Arg Asp Thr Ser Lys Asn Gln Tyr Tyr Leu
65                  70                  75                  80

Gln Leu Asn Ser Val Thr Thr Glu Asp Thr Ala Ile Tyr Tyr Cys Ala
                85                  90                  95

Arg Trp Leu Gly Gly Arg Ala Tyr Trp Gly Gln Gly Thr Thr Leu Ile
            100                 105                 110

Val Ser Ser
        115
```

<210> SEQ ID NO 18
<211> LENGTH: 107
<212> TYPE: PRT
<213> ORGANISM: Mus musculus
<220> FEATURE:
<223> OTHER INFORMATION: Variable region of mouse 8G7 light chain

<400> SEQUENCE: 18

```
Asp Ile Val Met Thr Gln Ser Gln Lys Phe Met Ser Thr Ser Val Gly
1               5                   10                  15
```

```
Asp Arg Val Ser Val Thr Cys Lys Ala Ser Gln Asn Val Gly Thr Asn
            20                  25                  30

Val Val Trp Tyr Gln Lys Pro Gly Gln Ser Pro Lys Thr Leu Ile
        35                  40                  45

Tyr Ser Ala Ser Arg Arg Phe Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Leu Lys
            100                 105
```

<210> SEQ ID NO 19
<211> LENGTH: 120
<212> TYPE: PRT
<213> ORGANISM: Mus musculus
<220> FEATURE:
<223> OTHER INFORMATION: Variable region of mouse 29C11 heavy chain

<400> SEQUENCE: 19

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Ile Trp Val Lys Gln Ala Pro Gly Lys Gly Leu Lys Trp Met
        35                  40                  45

Gly Trp Ile Asn Thr Tyr Thr Gly Lys Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Thr Glu Asp Thr Ala Thr Tyr Phe Cys
                85                  90                  95

Ala Arg Ser Asn Phe Arg Glu Asp Trp Cys Phe Asp Val Trp Gly Ala
            100                 105                 110

Gly Thr Thr Val Thr Val Ser Ser
        115                 120
```

<210> SEQ ID NO 20
<211> LENGTH: 106
<212> TYPE: PRT
<213> ORGANISM: Mus musculus
<220> FEATURE:
<223> OTHER INFORMATION: Variable region of mouse 29C11 light chain

<400> SEQUENCE: 20

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80
```

```
Asp Ala Ala Thr Tyr Tyr Cys Gln Gln Trp Ser Ser Asn Pro Pro Thr
            85                  90                  95

Phe Gly Ser Gly Thr Lys Leu Glu Ile Lys
            100                 105
```